United States Patent [19]

Sato et al.

[11] Patent Number: 4,493,943

[45] Date of Patent: Jan. 15, 1985

[54] ELECTRICAL INSULATING OIL AND OIL-FILLED ELECTRICAL APPLIANCES

[75] Inventors: Atsushi Sato, Tokyo; Keiji Endo, Yokohama; Shigenobu Kawakami, Ichikawa; Hitoshi Yanagishita; Shozo Hayashi, both of Yokohama, all of Japan

[73] Assignee: Nippon Petrochemicals Company, Limited, Japan

[21] Appl. No.: 533,263

[22] Filed: Sep. 16, 1983

[30] Foreign Application Priority Data

Sep. 16, 1982 [JP] Japan ................................. 57-161520
Jul. 12, 1983 [JP] Japan ................................. 58-126559

[51] Int. Cl.$^3$ .......................... H01B 3/24; H01B 9/06; H01F 27/12; H01G 4/22
[52] U.S. Cl. ............................ 174/25 C; 174/17 LF; 174/23 C; 252/570; 336/94; 361/317; 361/327; 585/1; 585/11; 585/25; 585/6.3; 585/6.6

[58] Field of Search ......... 252/570; 174/23 C, 17 LF, 174/25 C; 336/94; 361/317, 327; 585/1, 11, 25, 6.3, 6.6

[56] References Cited

U.S. PATENT DOCUMENTS 3,991,049 11/1976 Siegrist et al. ........................ 585/25
4,035,431 7/1977 Charbonneau ....................... 585/25
4,347,169 8/1982 Sato et al. ........................... 252/570

Primary Examiner—Paul Lieberman
Assistant Examiner—Robert A. Wax
Attorney, Agent, or Firm—Scully, Scott, Murphy & Presser

[57] ABSTRACT

An improved electrical insulating oil and oil-filled electrical appliances impregnated therewith. The electrical insulating oil is quite suitable for use in oil-filled electrical appliances in which insulating materials or dielectric materials made of plastics are employed. The electrical insulating oil comprises (a) at least one member of diarylalkanes and (b) at least one member selected from the group of mono- and/or diolefins having two condensed or noncondensed aromatic nuclei.

15 Claims, No Drawings

ELECTRICAL INSULATING OIL AND OIL-FILLED ELECTRICAL APPLIANCES

BACKGROUND OF THE INVENTION

1. Field of the Invention

This invention relates to an improved electrical insulating oil and oil-filled electrical appliances impregnated therewith.

More particularly, the invention relates to an electrical insulating oil and oil-filled electrical appliances in which the insulating oil comprises a mixture of diarylalkane and mono- and/or diolefin having two aromatic nuclei. The electrical insulating oil of the invention is quite suitable for use in oil-filled electrical appliances in which insulating materials or dielectric materials made of plastics such as polyolefins are employed.

2. Description of the Prior Art

Electrical appliances such as oil-filled capacitors, oil-filled power cables and transformers have recently been made to withstand high electric voltages while being small in size. With this tendency, various kinds of plastic films are used together with conventional insulating paper.

In the conventional art, refined mineral oils, polybutenes, alkylbenzenes, polychlorinated biphenyls and the like are used as electrical insulating oils; however, they have several drawbacks. For example, the use of polychlorinated biphenyls was discontinued because it constitutes a public health hazard. Furthermore, the conventional electrical insulating oils are not satisfactorily compatible with the foregoing plastic materials such as polyolefin films which are recently used in oil-filled electrical appliances.

With the requirements of high-voltage withstanding and size reduction, it is necessary that the electrical insulating oil has a high dielectric breakdown voltage, a low dielectric loss tangent, and good hydrogen gas absorbing capacity.

The hydrogen gas absorbing capacity indicates the stability of the insulating oil against corona discharge (partial discharge) under high electric voltage conditions. The higher the gas-absorbing capacity, the smaller the likelihood of corona discharge, which leads to the advantage of the insulating oil having excellent stability or durability.

Meanwhile, in order to meet the requirement of high-voltage use, plastic films such as polyolefin films, polystyrene films and polyester films are used to replace either partially or completely the conventional insulating paper as insulating materials or dielectric materials for electrical appliances such as oil-filled electric cables and capacitors. In view of their dielectric strength, dielectric loss tangent and dielectric constant, polyolefin films, especially polypropylene and cross-linked polyethylene films, are preferred as the plastic films.

When these polyolefin films are impregnated with insulating oils, some oils cause the films to swell to some extent. If a film becomes swollen, the thickness of the insulating layer increases. As a result, the resistance to the flow of insulating oil increases in electrical cables, and insufficient impregnation with insulating oil occurs in electric capacitors, causing the formation of voids (unimpregnated portions) and the undesirable lowering of the corona discharge voltage.

In connection with the above-mentioned conventional electrical insulating oils, the values of the dielectric breakdown voltages (BDV) and the dielectric loss tangents (tan δ) are satisfactory to a certain extent, but the hydrogen gas absorbing capacity or corona discharge characteristics and the stability of the dimensions of polypropylene films are not satisfactory.

BRIEF SUMMARY OF THE INVENTION

In view of the above-described conventional state of the art, it is the primary object of the present invention to provide an improved electrical insulating oil and oil-filled electrical appliances which are impregnated with the improved insulating oil and are free from the above-described disadvantages in the conventional art.

Another object of the present invention is to provide an electrical insulating oil which has an excellent dielectric constant and other electrical properties, which has a good hydrogen gas absorbing capacity, and which is highly compatible with plastic film insulating materials.

It is a further object of the present invention to provide oil-filled electrical appliances which have excellent corona discharge characteristics, dielectric breakdown voltage and other advantageous electrical characteristics, and have a long service life.

The present invention is, therefore, concerned with a novel and improved electrical insulating oil and electrical appliances which are impregnated therewith.

The electrical insulating oil of the invention comprises:

(a) at least one diarylalkane, and (b) at least one of mono- and/or diolefin having two condensed or noncondensed aromatic nuclei, excluding bicyclic monoolefins of unsaturated dimers and unsaturated codimers of styrenes such as styrene, α-methylstyrene and their monomethyl nuclear substituted compounds.

DETAILED DESCRIPTION OF THE INVENTION

The present invention will be described in more detail.

The alkane portion of the foregoing diarylalkane in item (a) is represented by a formula $-C_nH_{2n}-$, in which the symbol n is an integer preferably in the range of 1 to 10, or a cycloalkylene group. It is exemplified by divalent substituent groups which are obtained by removing two hydrogen atoms from methane, ethane, propane butane and cyclohexane. As the component of the electrical insulating oil of the invention, the diarylalkane in item (a) can be employed singly or in a mixture of two or more kinds and the viscosity of diarylalkane or a mixture of diarylalkanes is preferably not higher than 10 cSt at 40° C.

Exemplified as suitable diarylalkanes are dirylmethane, 1,1-diarylethane and 1,2-diarylethane, which are represented by the following general formulae (I), (II) and (III). Amoung these, any one having a benzene ring which is not substituted with an alkyl group, e.g. arylphenylethane is preferred. General formulae:

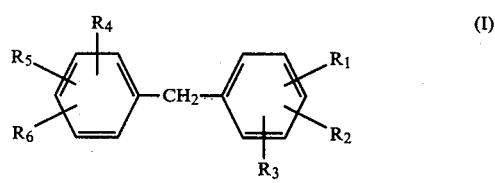

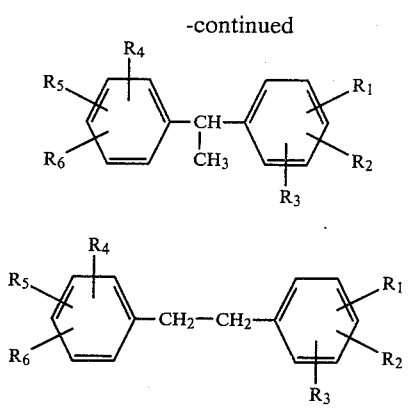

In the above general formulae (I) to (III), the symbols $R_1$, $R_2$, $R_3$, $R_4$, $R_5$ and $R_6$ represent a hydrogen atom or a methyl, ethyl, propyl, isopropyl, n-butyl, isobutyl, sec-butyl or tert-butyl group, and the total number of carbon atoms in the groups $R_1$ to $R_6$ is not more than 4.

The above diarylalkanes are exemplified by:
1,1-diphenylmethane, phenyl-methylphenylmethane,
1,1-(or 1,2-)diphenylethane,
1-phenyl-1-(or 2-)(methylphenyl)ethane,
1-phenyl-1-(or 2-)(dimethylphenyl)ethane,
1-phenyl-1-(or 2-)(ethylphenyl)ethane,
1-phenyl-1-(or 2-)(methylethylphenyl)ethane,
1-phenyl-1-(or 2-)(isopropylphenyl)ethane,
1-phenyl-1-(or 2-)(trimethylphenyl)ethane,
1-phenyl-1-(or 2-)(tert-butylphenyl)ethane,
1,1-(or 1,2-)di(methylphenyl)ethane,
1,1-(or 1,2-)di(ethylphenyl)ethane,
1,3-diphenybutane, 4-methyl-2,4-diphenylpentane,
4-methyl-2,4-di(methylphenyl)pentane, and
1-methyl-3-phenylindane.

These diarylalkanes can easily be prepared by reacting styrene or alkylstyrene with benzene or alkylbenzene in the presence of an acid catalyst. Further, these compounds can be obtained by separation from the byproduct in ethylbenzene preparation. Still further, they can be prepared by reacting a hydrocarbon halide such as benzyl chloride, 1,1-dichloroethane or 1,2-dichloroethane with benzene or alkylbenzene in the presence of a Friedel-Crafts catalyst. Also, they can be prepared by hydrogenating a linear unsaturated dimer of styrenes such as styrene, α-methylstyrene and isopropenyltoluene.

The compounds which are used together with the above-described diarylalkanes of item (a) are the compounds of the foregoing item (b), that is, mono- and/or diolefin having two condensed or noncondensed aromatic nuclei, excluding bicyclic monoolefins of unsaturated dimers and unsaturated codimers of styrenes such as styrene, α-methylstyrene and their monomethyl nuclear substituted compounds.

Incidentally, an electrical insulating oil comprising the foregoing diarylalkane of item (a) and the excluded portion of item (b), namely, "bicyclic monoolefins of unsaturated dimers and unsaturated codimers of styrenes such as styrene, α-methylstyrene and their monomethyl nuclear substituted compounds", is disclosed in U.S. Pat. No. 4,347,169 (Atsushi Sato, et al.). More particularly, the excluded compounds are represented by the following general formulae:

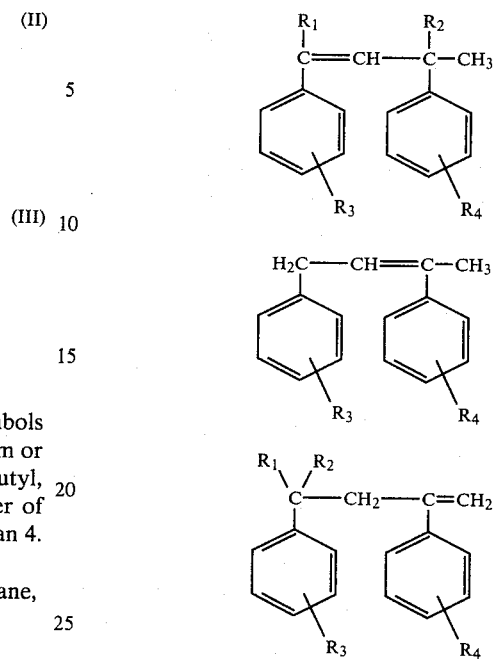

wherein each of $R_1$ to $R_4$ is a hydrogen atom or a methyl group and the total number of carbon atoms in $R_1$ to $R_4$ is an integer from zero to 2.

In the olefins of the above item (b), monoolefins having two aromatic nuclei are represented by the following general formulae (IV), (V) and (VI). General formula:

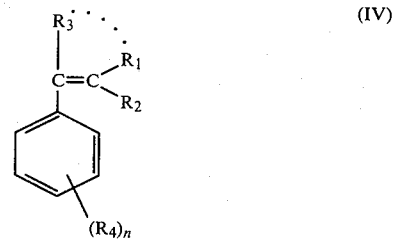

wherein any one of $R_1$, $R_2$, $R_3$ and $R_4$ is an aryl group or an aralkyl group and the others are a hydrogen atom or an alkyl group, respectively; n is an integer from 0 to 3; and when $R_4$ is an aryl group or an aralkyl group, n is 1. Further, the symbol "..." represents either the existence or nonexistence of a bond, and when it represents the existence of a bond, $R_1$ and $R_3$ are alkylene groups forming a 5- to 7-membered ring. As stated above, unsaturated dimers and unsaturated codimers of styrenes such as styrene, α-methylstyrene and their monomethyl nuclear substituted compounds are excluded. General formula:

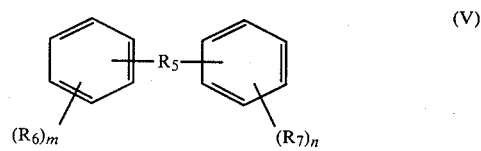

wherein $R_5$ is an alkenylene group or a cycloalkenylene group which is exemplified by a divalent substituent group obtained by removing two hydrogen atoms from olefininc hydrocarbons such as ethylene, propylene, butenes, cyclopentene and cyclohexene, and the aliphatic unsaturated double bond thereof is not conjugated with the aromatic nuclei. Further, m and n are representing integers from 0 to 3, and $R_6$ of m in number and $R_7$ of n in number are respectively the same or different from each other and each of them is a hydrogen atom or an alkyl group. General formula:

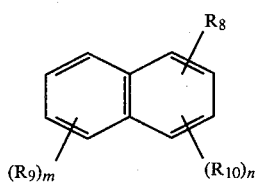

(VI)

wherein $R_8$ is ah alkenyl group or a cycloalkenyl group, m and n are representing integers from 0 to 3, and $R_9$ of m in number and $R_{10}$ of n in number are respectively the same or different from each other and each of them is a hydrogen atom or an alkyl group.

Among the aromatic olefins represented by the above formulae (IV) to (VI) which are used together with the diarylalkane of item (a), when $R_1$ or $R_2$ in formula (IV) is an aryl group or an aralkyl group, the compounds of formula (IV) are represented by the following general formula (IV-1), in which Ar denotes an aryl group or an aralkyl group. General formula:

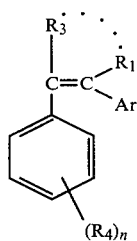

(IV-1)

In the case where $R_3$ is an aryl group or an aralkyl group in general formula (IV), the compounds are represented by the following general formula (IV-2).

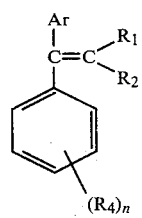

(IV-2)

Further, when $R_4$ is an aryl group or an aralkyl group in general formula (IV), the compounds are represented by the following general formula (IV-3).

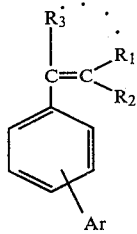

(IV-3)

In the above formulae (IV-1) to (IV-3), when Ar is an aryl group, it is exemplified by a phenyl, tolyl, xylyl, ethylphenyl, cumenyl group or the like. When Ar is an aralkyl group, Ar is, for example, a benzyl, 1- or 2-phenylethyl, 1- or 2-tolylethyl, 1- or 2-xylylethyl, 1- or 2-ethylphenylethyl, 1- or 2-cumenylethyl or 1-, 2- or 3-phenylpropyl group. In such cases, each of $R_1$ to $R_4$ in formulae (IV-1) to (IV-3) is a hydrogen atom or an alkyl group which is exemplified by a methyl, ethyl, propyl, isopropyl, n-butyl, isobutyl, sec-butyl or tert-butyl group. The symbol "..." in the above formula (IV-1) represents either the existence or nonexistence of a bond, and when it represents the existence of a bond, $R_1$ and $R_3$ are alkylene groups forming a 5- to 7-membered ring.

In the case where Ar is an aryl group in the above formula (IV-1), the compounds are exemplified by stilbene, 4-methylstilbene, 1,2-diphenylpropene-1, 1,2-diphenyl-1-methylpropene-1, 1,2-diphenylcyclohexene and 2,3-diphenylbutene-2.

In the case where Ar is an aralkyl group in the above formula (IV-1), the compounds are exemplified by 1,3-diphenylpropene, 1,4-diphenylbutene-1 and phenylbenzylcyclohexene.

In the case where Ar is an aryl group in the above formula (IV-2), the compounds are exemplified by 1,1-diphenylethylene, 1-phenyl-1-(4'-ethylphenyl)ethylene and 1,1-diphenylpropene-1.

In the case where Ar is an aralkyl group in the above formula (IV-2), the compounds are exemplified by 2,3-diphenylpropene and 1,2-diphenylbutene-2.

In the case where Ar is an aryl group in the above formula (IV-3), the compounds are exemplified by 2-isopropenylbiphenyl, 4-isopropenyl-biphenyl, 2-isopropenyl-4'-isopropylbiphenyl, cyclohexenyl-biphenyl and cyclopentenyl-biphenyl.

In the case where Ar is an aralkyl group in the above formula (IV-3), the compounds are exemplified by 1-phenyl-1-(4'-vinylphenyl)ethane, 1-(4-methylphenyl)-1-(4'-vinylphenyl)ethane, 1-phenyl-1-(4'-isopropenylphenyl)ethane, phenyl-(4'-vinylphenyl)methane and phenyl (cyclohexenylphenyl)methane.

In the foregoing general formula (V), the symbol $R_5$ is an alkenylene group or a cycloalkenylene group and the aliphatic unsaturated double bond of the group is not conjugated with any of the aromatic nuclei of the aromatic olefin. The $R_5$ is exemplified by butenylene, methylbutenylene, pentenylene, cyclopentenylene and cyclohexenylene. The symbols $R_6$ and $R_7$ denote a hydrogen atom or an alkyl group such as a methyl, ethyl, propyl, isopropyl, n-butyl, isobutyl, sec-butyl and tert-butyl group.

The aromatic olefins represented by the formula (V) are exemplified by 1,4-diphenylbutene-2, 1,4-diphenylpentene-2 and 1,4-diphenyl-2-methylpentene-2.

In the aromatic olefins represented by the general formula (VI), the symbol $R_8$ denotes an alkenyl group such as a vinyl, allyl, propenyl, isopropenyl and butenyl group, or a cycloalkenyl group such as a cyclopentenyl and cyclohexeneyl group. The symbols $R_9$ and $R_{10}$ denote a hydrogen atom or an alkyl group such as a methyl, ethyl, propyl, isopropyl, n-butyl, isobutyl, sec-butyl and tert-butyl group.

The aromatic olefins represented by the general formula (VI) are exemplified by α-vinylnaphthalene, isopropenylnaphthalene, allylnaphthalene and 1-cyclopent-2-enylnaphthalene.

In the aromatic olefins of the foregoing item (b) which are components of the electrical insulating oil of the present invention, the diolefins having two aromatic nuclei are represented by the following general formulae (VII), (VIII) and (IX). General formulae:

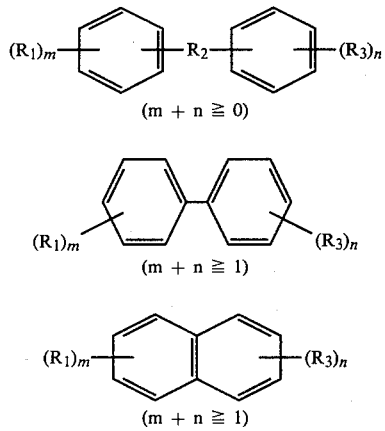

wherein $R_1$, $R_2$ and $R_3$ are hydrocarbon residual groups, respectively; each of m and n is 0 (zero) or a positive integer; $R_1$ of m in number, $R_2$, and $R_3$ of n in number are either the same or different substituent groups; and the total number of double bonds in the substituent groups is 2 in each formula.

In the case where $R_1$ or $R_3$ is an unsaturated group, it is an alkenyl or cycloalkenyl group, and is exemplified by a vinyl, propenyl, isopropenyl, allyl, butenyl, and cyclohexenyl group.

In the case where $R_1$ or $R_3$ is a saturated group, it is an alkyl or cycloalkyl group, and is exemplified by a methyl, ethyl, n-propyl, isopropyl, n-butyl, isobutyl, sec-butyl, tert-butyl, pentyl and cyclohexyl group.

In the case where $R_2$ is an unsaturated group, it is an alkenylene or cycloalkenylene group, and is exemplified by a divalent substituent group which is obtained by removing two hydrogen atoms from an olefinic hydrocarbon such as ethylene, propylene, butenes, cyclopentene, and cyclohexene.

Furthermore, in the case where $R_2$ is a saturated group, it is an alkylene or cycloalkylene group, and is exemplified by divalent substituent groups which are obtained by removing two hydrogen atoms from a saturated hydrocarbon such as methane, ethane, propane, butanes and cyclohexane.

The following compounds are exemplified as those represented by the foregoing formulae (VII), (VIII) and (IX). Compounds represented by formula (VII):

1-phenyl-1-(4'-vinylphenyl)ethylene; 1,1-diphenylbutadiene; 2,4-diphenyl-1,3-pentadiene; bis(4-isopropenylphenyl)methane; 1,1-bis(4-isopropenylphenyl)ethane; 1,2-bis(4-isopropenylphenyl)ethane; and 1,1-bis(vinylphenyl)ethane. Compounds represented by formula (VIII):

2,2'-divinylbiphenyl and 4,4'-diisopropenylbiphenyl. Compounds represented by formula (IX):

divinylnaphthalene and diisopropenylnaphthalene.

The above compounds are shown as examples of the components which can be used in the preparation of the insulating oil composition of the present invention, and the materials which may be used for the present invention are by no means restricted to the above exemplary compounds.

These aromatic olefins can be prepared by various chemical synthesis methods.

For instance, vinylnaphthalene is prepared by reacting formylnaphthalene with a Grignard reagent such as methylmagnesium iodide, and then dehydrating. Phenyl(vinylphenyl)ethane is prepared by reacting diphenylethane with acetyl chloride in the presence of a Friedel-Crafts catalyst to obtain phenyl(acetylphenyl)ethane, reducing by sodium borohydride, and then dehydrating. Phenyl(isopropenylphenyl)ethane is prepared by reacting phenyl(formylphenyl)ethane with a Grignard reagent such as methylmagnesium iodide, and then dehydrating. 1,2-Diphenylethylene is prepared by reacting benzaldehyde with benzylmagnesium bromide, and then dehydrating. 1,2-Diphenylpropene is also prepared by a similar method. 1,1-Diphenylethylene is prepared by reacting diphenyl ketone with a Grignard reagent such as methylmagnesium iodide, and then dehydrating.

Furthermore, the aromatic diolefins are prepared by obtaining a Grignard reagent having a vinyl group and an aromatic ring from, for example, bromostyrene, reacting the reagent with an aromatic ketone such as acetophenone, and dehydrating the obtained alcohol.

Still further, the aromatic olefins used in the present invention are prepared by employing reactions of dehydrogenation, oxidative dehydrodimerization and decomposition.

More particularly, in a method employing dehydrogenation, a saturated aromatic hydrocarbon corresponding to the aromatic monoolefin of the invention, or a saturated aromatic hydrocarbon or an aromatic monoolefin corresponding to the aromatic diolefin of the invention is dehydrogenated in the presence of a suitable dehydrogenation catalyst with suppressing side reactions of decomposition and polymerization.

In the reaction, the dehydrogenation catalyst is not restricted to any specific one. For example, the dehydrogenation catalysts are exemplified by one or a mixture of oxides of metals such as Cr, Fe, Cu, K, Mg and Ca or precious metals such as Pt and Pd, or these metal oxides or precious metals which are supported on a carrier such as alumina.

The reaction temperature of the dehydrogenation is in the range of 350° C. to 650° C., preferably 400° C. to 600° C. The LHSV (liquid hourly space velocity) of the dehydrogenation is in the range of 0.2 to 10, preferably 0.5 to 3.0. In the dehydrogenation; steam, nitrogen gas or hydrogen gas can be introduced into the reaction system in order to reduce partial pressures and to avoid the formation of carbon. Further, if necessary, a suitable diluent can be used. When the rate of dehydrogenation is not so high, raw materials themselves conveniently serve as a diluent.

Through the above procedures, for example, diphenylethylene is obtained from diphenylethane; vinylphenyl-phenylethane, from ethylphenyl-phenylethane; and vinylphenyl-phenylethylene, from ethylphenyl-phenylethylene. Further, isopropenyl biphenyl is obtained from isopropyl biphenyl; and isopropenyl-isopropylnaphthanene or diisopropenylnaphthalene, from diisopropylnaphthalene.

The aromatic monoolefins used in the present invention can also be prepared by oxidative dehydrodimerization method. In this method, methyl-substituted monocyclic aromatic hydrocarbon such as toluene, xylene, ethyltoluene and vinyltoluene are subjected to dimerization (coupling) together with dehydrogenation.

For example, 1,2-diphenylethylene is obtained from toluene, and 1,2-di(methylphenyl)ethylene, from xylene. In this reaction, a saturated aromatic hydrocarbon corresponding the obtained olefin, for example, 1,2-diphenylethane from toluene, is simultaneously obtained, which is convenient for preparing the electrical insulating oil of the present invention.

Any suitable catalyst can be used for this oxidative dehydrodimerization. For example, usable catalysts are copper chromite catalysts containing Ni, Ta or Ti as disclosed in Japanese Patent Publication No. 49-6312 (1974), the catalysts of oxides of metals such as Bi, Pb, Te, Ba, Tl and Cd or their mixture as disclosed in Japanese Patent Publication No. 49-20561 (1974), and composite oxide catalyst of Tl as disclosed in U.S. Pat. No. 4,243,825. Further, alkali metal oxides as promoters can be added to these catalysts.

This reaction can be carried out in the presence of molecular oxygen with the above-described catalyst. The molar ratio of oxygen/methyl-substituted aromatic hydrocarbon is in the range of 0.01 to 5.0, preferably 0.05 to 1.0. Meanwhile, the reaction can be performed stoichiometrically without the presence of molecular oxygen, in which oxidation treatment in addition to usual treatment to remove deposited carbon, is necessary because the oxide catalyst is reduced with the progress of reaction.

The reaction temperature is in the range of 300° C. to 800° C, and preferably 500° C. to 700° C. The contact time is in the range of 0.01 second to several minutes, and preferably 0.1 to 30 seconds. The pressure in this reaction is not restricted from a reduced pressure to 100 atmospheric pressure, but preferably in the range of 0.1 to 5.0 atmospheric pressure.

Further, the aromatic olefins used in the present invention can also be prepared by decomposition such as thermal cracking and catalytic cracking, in which, for example, triarylalkanes, diaralkyl aromatic hydrocarbons and polymers of styrenes are employed as raw materials.

In the thermal cracking of the above raw materials, the reaction temperature is set in the range of 300° C. to 700° C., and preferably in the range of 330° C. to 600° C. When the reaction temperature is too low, the rate of decomposition becomes very low. On the other hand, when the reaction temperature is too high, the raw material is decomposed to monocyclic hydrocarbons. Accordingly, in order to obtain the aromatic hydrocarbons used in the present invention at a higher yield, it is advisable that the thermal cracking is performed at a relatively higher temperature with a shorter retention time.

In the catalytic cracking, silica, silica gel, silica-alumina, kaolin, zeolite (with or without de-aluminum treatment), and organic or inorganic sulfonic acid can be used. The reaction is preformed in a liquid phase or gas phase, and the reaction temperature is in the range of 300° C. to 700° C., and preferably in the range of 330° C. to 600° C.

The above-mentioned monoolefin and/or diolefin having two condensed or noncondensed aromatic nuclei is/are employed as a mixture with the diarylalkane. Accordingly, provided the monoolefin and/or diolefin can be mixed and dissolved into the diarylalkane and produces a liquid mixture at ordinary temperatures, the olefin itself can be either liquid or solid. The above olefin having two aromatic nuclei can be used singly or in a mixture of two or more kinds together with the diarylalkane.

In the present application, as described above, the electrical insulating oil is prepared by mixing the diarylalkane of (a) and the aromatic olefin of (b). The viscosity of the thus prepared insulating oil of the invention is preferably not higher than 30 cSt and more preferably not higher than 10 cSt at 40° C. Accordingly, in order to obtain a mixture having a viscosity of the above value, components are suitably selected from the compounds of formulae (I) to (III) as diarylalkanes of (a) and from the foregoing compounds as aromatic olefins of (b).

Although the diarylalkanes themselves have excellent electrical properties and good biodegradability, thermal stability and oxidation stability, when they are used in a mixture with the aromatic olefins of the present invention, the hydrogen gas absorbing capacity can be further improved. In addition, in spite of the mixing with the unsaturated compounds of the aromatic olefins, no deterioration in biodegradability, thermal stability and oxidation stability is observed in practical uses, while various electrical properties can be improved.

The mixing ratio of the diarylalkane of (a) and the aromatic olefin of (b) is arbitrary. However, a ratio of 0.01 to 50% by weight of the aromatic olefin with respect to the mixture of both component materials is preferable in view of their synergistic effects. The more preferable quantity of the aromatic olefin is 1.0 to 30% by weight.

The electrical insulating oil of the present invention is made of a mixture having the above-described composition; however, the present invention is not restricted to the foregoing composition. That is, in order to improve desired electrical characteristics without impairing the general electrical properties, other conventional electrical insulating oils such as polybutene, mineral oils, alkylbenzenes, alkylnaphthalenes and alkylbiphenyls can be added to the insulating oil of the present invention. When polybutene is added, the volume resistivity and dielectric loss tangent can be improved. The addition of mineral oils can improve the dielectric breakdown voltage, and the addition of alkylbenzenes or other aromatic insulating oils can improve the dielectric breakdown voltage, dielectric loss tangent and pour point.

In order to improve further the oxidation stability, several known antioxidants can be added to the electrical insulating oil of the present invention. As such antioxidants, there are phenol compounds such as 2,6-di-tert-butyl-p-cresol, 2,2'-methylenebis(4-methyl-6-tert-butylphenol), 4,4'-butylidenebis(3-methyl-6-tert-butylphenol), 4,4'-thiobis(3-methyl-6-tert-butylphenol), stearyl-β-(3,5-di-tert-butyl-4-hydroxyphenol)propionate, tetrakis[methylene-3(3', 5'-di-tert-butyl-4'-hydroxyphenyl)-propionate]methane, 1,3,5-trimethyl-2,4,6-tris(3,5-di-tert-butyl-4-hydroxybenzyl)benzene, and 1,1,3-tris(2-methyl-4-hydroxy-5-tert-butylphenol)butane; sulfur compounds such as dilauryl thiodipropionate, distearyl thiodipropionate, laurylstearyl thiodipropionate, and dimyristyl thiodipropionate; and phosphorous compounds such as triisodecylphosphite, diphenylisodecylphosphite, triphenylphosphite, and trinonylphenylphosphite.

These antioxidants can be added to the electrical insulating oil singly or in combination of two kinds or more. The addition quantity of the antioxidant is 0.001 to 5% by weight and preferably 0.01 to 2.0% by weight of the electrical insulating oil.

Furthermore, in order to impart a nonflammable property and other desirable effects to the electrical insulating oil of the present invention, several known additives such as phosphoric esters and epoxy compounds can be added to the electrical insulating oil.

The electrical insulating oil of the present invention is good for general uses and, in particular, it is advantageous for the impregnation of oil-filled electrical appliances such as electric capacitors, power cables and transformers.

As described at the beginning of this specification, the requirements of high-voltage withstanding and size reduction of such oil-filled electrical appliances have become severe in recent years. In order to meet these requirements, plastics are used to replace either partially or totally the conventional insulating paper as insulating materials or dielectric materials for the oil-filled electrical appliances. More particularly, as electrical insulating materials (dielectric materials) of electric capacitors, there is proposed the use of a combination of insulating paper and plastic films such as stretched or nonstretched polypropylene, polymethylpentene, or polyester film; the use of these plastic films singly; the use of embossed films of these plastic films to facilitate impregnation with the insulating oil; or the use of metallized plastic films, wherein the metallic layer serves as an electrode. In the case of oil-filled cables, the electrical insulating materials are made of polyolefin film such as cross-linked or non-cross-linked polyethylene film, stretched or nonstretched polypropylene film, and polymethylpentene film; paper-polyolefin laminated film made by the extrusion of polyolefin onto paper; composite film which is made by cross-linking insulating paper with silane-grafted polyethylene in the presence of a silanol condensation catalyst; or an artificial paper sheet which is made by mixing wood pulp and polyolefin fiber.

The electrical insulating oil of the present invention is excellent in compatibility with plastic materials. Accordingly, the electrical insulating oil is quite suitable for use in oil-filled electrical appliances such as electric capacitors and electric cables in which plastic materials are used for either part or all of the insulating material or dielectric material.

More particularly, when an electric capacitor is provided with an insulating (dielectric) material that is partially or totally made of plastics, especially polyolefin, and when it is impregnated with the electrical insulating oil of the present invention, the insulating material can be fully and completely impregnated with the electrical insulating oil because swelling of the insulating material is slight, and voids (unimpregnated portions) are not formed. Accordingly, corona discharge due to the convergence of electric fields to the voids hardly occurs, and dielectric breakdown can be well avoided. Furthermore, the electrical insulating oil of the present invention has excellent hydrogen gas absorbing capacity and corona discharge resistance under high-voltage stress, so that it is possible to obtain both a long service life and high-voltage use of the electrical appliances.

In the case of electric power cables, a change in dimensions of the insulating material due to swelling is small, and resistance to the insulating oil flow can be made low so that oil impregnation can be performed in a short time. Of course, it will be understood that, because of the ease of impregnation, voids are hardly formed and the dielectric breakdown voltage becomes higher. When a cable is made by using an insulating material of a laminated film or composite film made of plastic material and paper, peeling, creasing and buckling of the insulating material upon bending of the cable do not occur even when the insulating material has been in contact with the electrical insulating oil for a long time. Further, as in the case of the electric capacitor, a power cable having a good corona discharge resistance can be obtained due to the excellent hydrogen gas absorbing capacity of the electrical insulating oil. Accordingly, it is also possible to obtain a long service life and high-voltage use, as for the capacitors.

According to the present invention, the above-described advantageous features can be improved by impregnation with the electrical insulating oil consisting of a plurality of specific component materials, owing to the synergistic effect between the component materials. Further, the good electrical characteristics, biodegradability, thermal resistance, and oxidation stability of each component material can be well maintained, and at the same time, the viscosity and pour point of the electrical insulating oil composition can be adjusted within desired ranges. Therefore, the manufacture of oil-filled electrical appliances is facilitated, and oil-filled electrical appliances exhibiting high performance under any use conditions can be obtained.

In the following, the electrical insulating oil and electrical appliances impregnated therewith according to the present invention will be described in more detail with reference to several examples.

EXAMPLES

The monoolefin and/or diolefin having two condensed or noncondensed aromatic nuclei of the present invention can be prepared by several known methods as described above. For reference purposes, however, the preparation of some of compounds of item (b) employed in the following Examples will be described.

PREPARATION EXAMPLE 1

Preparation of 1-phenyl-1-(4'-vinylphenyl)ethane

Synthesis of Ketone

To a 5 liter reaction vessel equipped with a stirrer, reflux condenser and dropping funnel were added 2 liters of carbon tetrachloride and 475 g of anhydrous aluminum chloride, and the contents were cooled by ice while being stirred. This was followed by the addition of 275 g of acetyl chloride through the dropping funnel and additional stirring for 1 hour. To this was added 546 g of 1,1-diphenylethane, and the contents were stirred for 4 hours. After the reaction, the aluminum chloride was deactivated by diluted hydrochloric acid and the reaction mixture was rinsed with an aqueous solution of sodium carbonate. The reaction medium was then removed by distillation to obtain 502 g of ketone in a yield of 74.7 %.

Synthesis of Alcohol

To a 2 liter reaction vessel equipped with a stirrer, reflux condenser and dropping funnel were added 600 ml of isopropyl alcohol and 84 g of sodium borohydride, and the isopropyl alcohol was refluxed by heating the vessel. The ketone (500 g) was added dropwise for 1 hour to this mixture and the reaction mixture was stirred further with refluxing of the isopropyl alcohol.

After the reaction, the catalyst was deactivated by adding water. The reaction product was separated by ether extraction and was dried by anhydrous sodium sulfate. The ether was distilled off to obtain 480 g of alcohol in a yield of 95.2%.

Synthesis of 1-phenyl-1-(4'-vinylphenyl)ethane

A 500 ml three neck flask was equipped with a dropping funnel, 40 g of potassium hydrogensulfate was fed into the flask, and it was heated to 230° C. to 240° C. under a reduced pressure. The above-obtained alcohol (480 g) was then added through the dropping funnel. The alcohol was dehydrated to produce an olefin, which olefin was immediately collected by distillation into an outer receptacle. By removing water from the obtained olefin, 332 g of 1-phenyl-1-(4'-vinylphenyl)ethane was obtained in a yield of 75.2% (b.p. 149° C./10 mmHg, 113° C./2 mmHg).

The chemical structure of the final product was identified by elemental analysis, IR spectrum analysis and NMR spectrum analysis.

PREPARATION EXAMPLE 2

Preparation of 1-phenyl-1-(4'-isopropenylphenyl)ethane

Synthesis of Alcohol

To a 5 liter reaction vessel equipped with a stirrer, reflux condenser and dropping funnel were added 71 g of metallic magnesium and 2 liters of diethyl ether, which was dried by metallic sodium. While cooling the contents by ice with stirring, 410 g of methyl iodide was slowly added dropwise, which was followed by the dropping of 500 g of a ketone [1-phenyl-1-(4'-acetylphenyl)ethane]obtained in like manner as in the foregoing Preparation Example 1. After the above dropwise addition, the mixture was allowed to react for 30 min. with stirring. Following the reaction, the reaction mixture was poured into a mixture of iced water and sulfuric acid to recover the layer of ether. After that, the ether was evaporated off to obtain 495 g of alcohol in a yield of 92.4%.

Synthesis of 1-phenyl-1-(4'-isopropenylphenyl)ethane

In like manner as in the foregoing Preparation Example 1, the above 495 g of alcohol was dehydrated to produce 310 g of 1-phenyl-1-(4'-isopropenylphenyl)ethane in a yield of 67.7% (b.p. 153° C./10 mmHg, 116° C./2 mmHg).

The chemical structure of the final product was identified by elemental analysis, IR spectrum analysis and NMR spectrum analysis.

PREPARATION EXAMPLE 3

Preparation of 1-(4-tert-butylphenyl)-1-(4'-vinylphenyl)ethane

A 5 liter separable flask equipped with a stirrer, reflux condenser and dropping funnel was fed with 1340 g (10 moles) of tert-butylbenzene and 3 ml of trifluoromethane sulfonate, and the contents were maintained at 50° C. to 60° C. While stirring, 104 g (1 mole) of styrene was then added dropwise for 2 hours and, after the addition, the stirring was continued for further 30 minutes. After the reaction, the catalyst was deactivated with water and, through neutralization, water rinsing, drying and distillation, 1-phenyl-1-(4'-tert-butylphenyl)ethane was obtained.

In like manner as in Preparation Example 1, 200 g of this 1-phenyl-1-(4'-tert-butylphenyl)ethane was reacted with acetyl chloride to obtain 1-(4-acetylphenyl)-1-(4'-tert-butylphenyl)ethane. Also in like manner as in Preparation Example 1, this compound was converted into an alcohol by using sodium borohydride, and the product was then dehydrated with potassium hydrogensulfate to obtain 1-(4-tert-butylphenyl)-1-(4'-vinylphenyl)ethane in a yield of 69.2% (b.p. 171° C./10 mmHg, 130° C./2 mmHg).

The chemical structure of the final product was identified by elemental analysis, IR spectrum analysis and NMR spectrum analysis.

PREPARATION EXAMPLE 4

Preparation of 1-(3-methylphenyl)-1-(3'-methyl-4'-vinylphenyl)ethane

A starting material of 1,1-di-m-tolylethane was reacted with acetyl chloride in like manner as in Preparation Example 1 to obtain a ketone. This ketone was converted into an alcohol by using sodium borohydride. The alcohol was dehydrated with sodium hydrogensulfate and distilled under reduced pressure to obtain 1-(3-methylphenyl)-1-(3'-methyl-4'-vinylphenyl)ethane in a yield of 67.1% (b.p. 164° C./10 mmHg, 123° C./2 mmHg).

The chemical structure of the final product was identified by elemental analysis, IR spectrum analysis and NMR spectrum analysis.

PREPARATION EXAMPLE 5

Preparation of 1-phenyl-1-(4'-vinylphenyl)ethylene

A Grignard reagent was prepared by adding 14.6 g (0.601 mole) of magnesium to 250 ml of dried tetrahydrofuran, heating the mixture to 65° C., and adding dropwise 100 g (0.546 mole) of p-bromostyrene. This reagent was then cooled to 20° C. and 65.5 g (0.546 mole) of acetophenone was added dropwise to the reagent. The reaction mixture was placed in a mixture of 500 g of crushed ice, 500 g of water and 15 ml of 98% sulfuric acid.

After that, a reaction product of alcohol was obtained by ether extraction. This alcohol was then dehydrated by potassium hydrogensulfate to obtain 62.8 g of 1-phenyl-1-(4'-vinylphenyl)ethylene in a yield of 56%, which compound was liquid at ordinary temperatures (b.p. 151° C./10 mmHg, 114° C./2 mmHg).

The chemical structure of the final product was identified by elemental analysis, IR spectrum analysis and NMR spectrum analysis.

PREPARATION EXAMPLE 6

Preparation of a Mixture of Aromatic Olefins

1-Phenyl-1-(4'-ethylphenyl)ethane was dehydrogenated in the presence of a catalyst and steam under the following conditions and obtained an oil of the following composition.

Conditions of Dehydrogenation:
Catalyst: Iron oxide catalyst containing promoters of potassium carbonate and chromium oxide Trade mark: G64A, made by Nissan Girdler Catalyst Co., Ltd. Particle size: 14 –28 mesh
Temperature: 550°C.
LHSV: 1.0
$H_2O$/Starting Material (by weight): 3.0
Pressure: Atmospheric pressure
Composition of the Obtained Oil:

| Compounds | % by weight |
|---|---|
| 1-phenyl-1-(4'-ethylphenyl)ethane | 23.8 |
| 1-phenyl-1-(4'-ethylphenyl)ethylene | 39.9 |
| 1-phenyl-1-(4'-vinylphenyl)ethane | 5.0 |
| 1-phenyl-1-(4'-vinylphenyl)ethylene | 28.1 |
| Others | 3.2 |
| Total | 100.0 |

EXAMPLES 1 to 25

(A) Formulation of Electrical Insulating Oils and Their Electrical Characteristics Samples of electrical insulating oils were prepared according to the compositions indicated in the following Table 1. In this Table, Examples 1, 17, 19, 20 and 21 are comparative examples and others are examples according to the present invention.

In all examples, 0.2% by weight of BHT (2,6-di-tert-butyl-p-cresol) was added to the electrical insulating oils as antioxidant. The viscosities of all insulating oils became within the range of 4.5 to 6.5 cSt at 40° C.

The electrical insulating oils were subjected to electrical charcteristics tests, the results of which are shown in the following Table 2. The tests were performed in accordnace with JIS C 2101 (Methods for Testing Electrical Insulating Oil).

TABLE 1

| Example No. | Diarylalkane Name | wt. % | Aromatic Olefin Name | wt. % |
|---|---|---|---|---|
| 1 | 1-Phenyl-1-xylylethane | 100 | — | — |
| 2 | " | 90 | 1-Phenyl-1-(4'-vinylphenyl)ethane | 10 |
| 3 | " | 90 | 1-(4-Methylphenyl)-1-(4'-vinylphenyl)-ethane | 10 |
| 4 | " | 90 | 1-Phenyl-1-(4'-isopropenylphenyl)-ethane | 10 |
| 5 | " | 90 | Phenyl-(4'-vinylphenyl)methane | 10 |
| 6 | " | 90 | 2-Isopropenylbiphenyl | 10 |
| 7 | " | 90 | α-Vinylnaphthalene | 10 |
| 8 | " | 95 | trans-Stilbene | 5 |
| 9 | " | 90 | 4-Methylstilbene | 10 |
| 10 | " | 90 | 1,2-Diphenylpropene-1 | 10 |
| 11 | " | 95 | 1,1-Diphenylethylene | 5 |
| 12 | " | 90 | " | 10 |
| 13 | " | 80 | " | 20 |
| 14 | " | 90 | 1-Phenyl-1-(4'-ethylphenyl)ethylene | 10 |
| 15 | " | 90 | 1,4-Diphenylbutene-2 | 10 |
| 16 | 1-Phenyl-1-xylylethane | 90 | 1-Cyclopent-2-enylnaphthalene | 10 |
| 17 | 1-Phenyl-2-(4'-isopropylphenyl)ethane | 100 | — | — |
| 18 | 1-Phenyl-2-(4'-isopropylphenyl)ethane | 90 | 1,1-diphenylethylene | 10 |
| 19 | 1-Phenyl-1-xylylethane | 90 | 1-Hexadecene | 10 |
| 20 | " | 90 | 1,3-Diphenylbutene-1 | 10 |
| 21 | " | 90 | 2,4-Diphenyl-4-methylpentene-1 | 10 |
| 22 | " | 90 | 1-(4-tert-Butylphenyl)-1-(4'-vinylphenyl)ethane | 10 |
| 23 | " | 90 | 1-(3-Methylphenyl)-1-(3'-methyl-4'-vinylphenyl)ethane | 10 |
| 24 | " | 90 | 1-Phenyl-1-(4'-vinylphenyl)ethylene | 10 |
| 25 | " | 82 | Mixed aromatic olefin of Preparation Example 6 | 18 |

TABLE 2

| Test Item | Example No. 1 | 2 | 6 | 7 | 11 | 13 | 20 | 25 |
|---|---|---|---|---|---|---|---|---|
| Flash Point (PMCC, °C.) | 155 | 154 | 152 | 151 | 151 | 149 | 156 | 155 |
| Pour Point (°C.)* | <−50 | <−50 | <−50 | <−50 | <−50 | <−50 | <−50 | <−50 |
| Kinematic Viscosity (cSt, at 37.8° C.) | 5.1 | 5.0 | 5.0 | 4.9 | 5.0 | 4.8 | 5.4 | 5.0 |
| Dielectric Breakdown Voltage (kV/2.5 mm)** | >70 | >70 | >70 | >70 | >70 | >70 | >70 | >70 |
| Dielectric Loss Tangent (%, at 80° C.) | 0.022 | 0.019 | 0.020 | 0.015 | 0.011 | 0.018 | 0.015 | 0.013 |
| Volume Resistivity | 7.8 × | 9.8 × | 9.5 × | 8.0 × | 1.0 × | 8.3 × | 8.1 × | 8.9 × |

TABLE 2-continued

| | Electrical Characteristics | | | | | | | |
|---|---|---|---|---|---|---|---|---|
| | Example No. | | | | | | | |
| Test Item | 1 | 2 | 6 | 7 | 11 | 13 | 20 | 25 |
| (Ωcm, at 80° C.) | $10^{14}$ | $10^{14}$ | $10^{14}$ | $10^{14}$ | $10^{15}$ | $10^{14}$ | $10^{14}$ | $10^{14}$ |
| Dielectric Constant | 2.49 | 2.49 | 2.52 | 2.53 | 2.50 | 2.52 | 2.50 | 2.52 |

Notes:
*<−50 means "not higher than −50".
**>70 means "larger than 70".

(B) Adaptability of Insulating Oils to Polypropylene Film

The adaptability of insulating oils in Table 1 to polypropylene film was tested.

A polypropylene film of 14 μin thickness was cut into a certain configuration and each cut film was immersed into each insulating oil at 80° C. for 72 hours. After that the cut film was taken out and the ratio of change in volume (%) of before and after the immersion was measured.

The results of this test are shown in the following Table 3, in which if the resultant value is small, i.e. the ratio of volume change is small, the tendency to swell the polypropylene film is small giving good size stability of the polypropylene film, and it is understood that the adaptability of the insulating oil to the polypropylene is good.

As will be understood from the results shown in Table 3, the electrical insulating oils according to the present invention have good adaptability with regard to polypropylene. Meanwhile, the insulating oil of Example 19 containing an aliphatic olefin such as 1-hexadecene has a large ratio of volume change, from which it will be understood that this oil has not adaptability to polypropylene.

(C) Test of Oil-Filled Capacitor

Two sheets of polypropylene films (thickness: 14 μ) which were the same kind as those used in the above test, were put together in layers to obtain a dielectric material. The dielectric material and aluminum foil as an electrode were wound together according to the conventional method to obtain model capacitors for oil impregnation.

These model capacitors were impregnated with the foreging electrical insulating oils in vacuum to prepare oil-filled capacitors of about 0.4 μF electrostatic capacitance.

The corona starting voltages (CSV) and corona ending voltages (CEV) were then measured by applying electric valtages to the capacitors thus prepared. The temperature of measuring was 30° C. and the results of measurement are also shown in the following Table 3.

Meanwhile, similar oil-filled capacitors were applied with a constant alternating voltage until the capacitors were broken to measure breakdown times. The results thereof are also shown in the following Table 3, in which each value was calculated such that seven capacitors impregnated with the same oil were tested and the maximum value and minimum value were neglected and the average of other 5 breakdown times was adopted as the resultant value.

TABLE 3

| Example No. | Ratio of Volume Change (%) | CSV (kV) | CEV (kV) | Breakdown Time (× 1000 sec.) |
|---|---|---|---|---|
| 1 | 7.2 | 2.8 | 2.2 | 1.0 |
| 2 | 7.7 | 3.2 | 2.6 | 39.8 |
| 3 | 7.1 | 3.2 | 2.6 | 37.1 |
| 4 | 7.1 | 3.2 | 2.6 | 20.3 |
| 5 | 7.0 | 3.2 | 2.6 | 42.2 |
| 6 | 7.1 | 3.2 | 2.6 | 18.4 |
| 7 | 7.2 | 3.2 | 2.6 | 25.5 |
| 8 | 7.0 | 3.0 | 2.5 | 4.2 |
| 9 | 7.0 | 3.1 | 2.5 | 9.3 |
| 10 | 7.1 | 3.1 | 2.5 | 8.9 |
| 11 | 7.2 | 3.0 | 2.5 | 9.8 |
| 12 | 7.4 | 3.1 | 2.5 | 21.0 |
| 13 | 7.4 | 3.3 | 2.6 | 27.2 |
| 14 | 7.3 | 3.1 | 2.5 | 18.3 |
| 15 | 7.5 | 3.1 | 2.4 | 4.8 |
| 16 | 7.2 | 3.0 | 2.5 | 5.9 |
| 17 | 7.4 | 2.6 | 2.1 | 0.7 |
| 18 | 7.5 | 3.0 | 2.4 | 6.8 |
| 19 | 11.6 | — | — | — |
| 20 | 7.2 | 2.9 | 2.3 | 3.0 |
| 21 | 7.1 | 3.0 | 2.4 | 3.2 |
| 22 | 7.7 | 3.2 | 2.6 | 28.0 |
| 23 | 7.4 | 3.2 | 2.6 | 30.5 |
| 24 | 7.1 | 3.4 | 2.8 | 41.3 |
| 25 | 7.1 | 3.3 | 2.7 | 29.8 |

From the results shown in Table 3, it will be understood that the values of both CSV and CEV of the capaciotors impregnated with the insulating oil of the present invention are all higher than the values of capacitors impregnated with the oils of Examples 1 and 17 which consists of singly diarylalkane and that the life of the former capacitors can be much prolonged. Furthermore, it is quite apparent that the expected life of the capacitors prepared according to the present invention is quite excellent as compared with the capacitors which are impregnated with the oils of Example 20 and 21 (containing linear unsaturated dimers of styrene or α-methylstyrene).

As described above, the electrical insulating oil of the present invention is excellent in the adaptability to plastic films, improved in the dielectric strength, and quite stable to the energy of electric discharge. Especially, the electrical insulating oil of the present invention can be advantageously used for the electrical appliances containing the insulating (dielectric) material at least partially made of polyolefin film or the like.

What is claimed is:

1. An electrical insulating oil comprising:
   (a) at least one member of diarylalkanes, and
   (b) at least one member selected from the group of monolefins, diolefins and mixtures thereof having two condensed or noncondensed aromatic nuclei, excluding bicyclic monoolefins of unsaturated dimers and unsaturated codimers of styrenes such as styrene, α-methylstyrene and their monomethyl nuclear substituted compounds.

2. The electrical insultaing oil in claim 1, wherein the mixing ratio of said aromatic mono- and diolefins is in the range of 0.01 to 50% by weight.

3. The electrical insultaing oil in claim 1, wherein the viscosity of said electrical insulating oil is not higher than 30 cSt at 40° C.

4. The electrical insulating oil in claim 1, wherein said diarylalkanes are the compounds represented by the following general formulae (I) to (III):

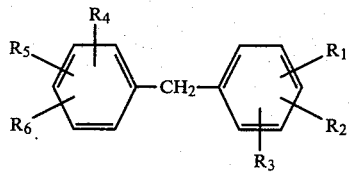
(I)

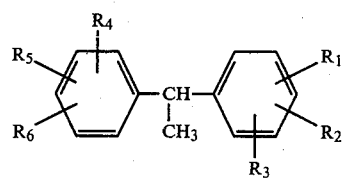
(II)

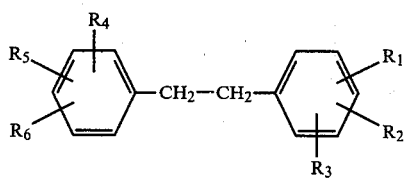
(III)

wherein each of the symbols $R_1$, $R_2$, $R_3$, $R_4$, $R_5$ and $R_6$ represents a hydrogen atom or a methyl, ethyl, propyl, isopropyl, n-butyl, isobutyl, sec-butyl or tert-butyl group, and the total number of carbon atoms in the groups $R_1$ to $R_6$ is not more than 4.

5. The electrical insultaing oil in claim 1, wherein said aromatic monoolefins are the compounds represented by the following general formulae (IV) to (VI):

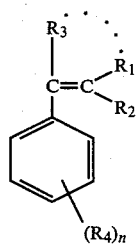
(IV)

wherein any one of $R_1$, $R_2$, $R_3$ and $R_4$ is an aryl group or an aralkyl group and the others are a hydrogen atom or an alkyl group, n is an integer from 0 to 3, when $R_4$ is an aryl group or an aralkyl group, n is 1, the symbol "....." represents either the existence or nonexistence of a bond, and when it represents the existence of a bond, $R_1$ and $R_3$ are alkylene groups forming a 5- to 7-membered ring.

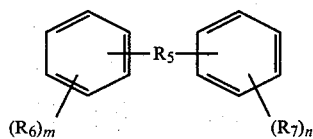
(V)

wherein $R_5$ is an alkenylene group or a cycloalkenylene group, and the aliphatic unsaturated double bond thereof is not conjugated with the aromatic nuclei, m and n are integers from 0 to 3, and $R_6$ of m in number and $R_7$ of n in number are the same or different from each other and each of them is a hydrogen atom or an alkyl group.

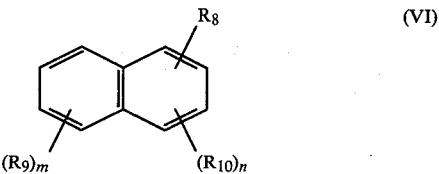
(VI)

wherein $R_8$ is an alkenyl group or a cycloalkenyl group, m and n are integers from 0 to 3, $R_9$ of m in number and $R_{10}$ of n in number are the same or different from each other, and each of them is a hydrogen atom or an alkyl group.

6. The electrical insultaing oil in claim 1, wherein said aromatic diolefins are the compounds represented by the following general formulae (VII) to (IX):

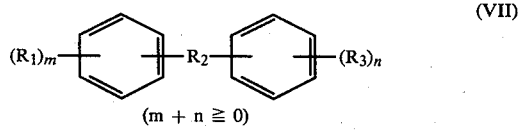
(VII)

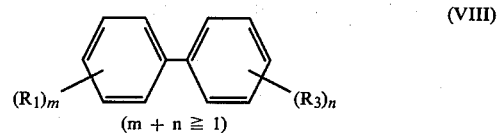
(VIII)

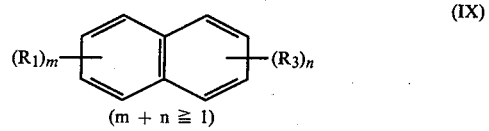
(IX)

wherein $R_1$, $R_2$ and $R_3$ are hydrocarbon residual groups, each of m and n is 0 (zero) or a positive integer, $R_1$ of m in number, $R_2$, and $R_2$ of n in number are either the same or different substituent groups, and the total number of double bonds in the substituent groups is 2 in each formula.

7. An oil-filled electrical appliance which is impregnated with an electrical insulating oil comprising:
(a) at least one member of diarylalkanes, and
(b) at least one member selected from the group of monoolefins, diolefins and mixtures thereof having two condensed or noncondensed aromatic nuclei, excluding bicyclic monoolefins of unsaturated dimers and unsaturated codimers of styrenes such as styrene, α-methylstyrene and their monomethyl nuclear substituted compounds.

8. The oil-filled electrical appliance in claim 7, wherein the mixing ratio of said aromatic monoand diolefins is in the range of 0.01 to 50% by weight.

9. The oil-filled electrical appliance in claim 7, wherein the viscosity of said electrical insulating oil is not higher than 30 cSt at 40° C.

10. The oil-filled electrical appliance in claim 7, wherein said diarylalkanes are the compounds represented by the following general formulae (I) to (III):

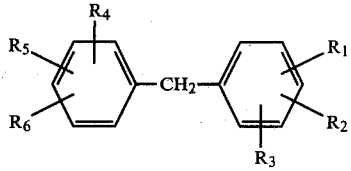
(I)

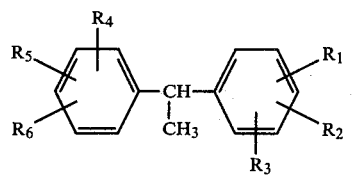
(II)

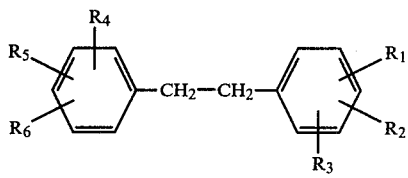
(III)

wherein each of the symbols $R_1$, $R_2$, $R_3$, $R_4$, $R_5$ and $R_6$ represents a hydrogen atom or a methyl, ethyl, propyl, isopropyl, n-butyl, isobutyl, sec-butyl or tert-butyl group, and the total number of carbon atoms in the groups $R_1$ to $R_6$ is not more than 4.

11. The oil-filled electrical appliance in claim 7, wherein said aromatic monoolefins are the compounds represented by the following general formulae (IV) to (VI):

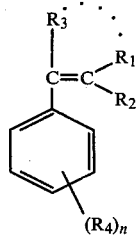
(IV)

wherein any one of $R_1$, $R_2$, $R_3$ and $R_4$ is an aryl group or an aralkyl group and the others are a hydrogen atom or an alkyl group, n is an integer from 0 to 3, when $R_4$ is an aryl group or an aralkyl group, n is 1, the symbol "......" represents either the existence or nonexistence of a bond, and when it represents the existence of a bond, $R_1$ and $R_3$ are alkylene groups forming a 5- to 7-membered ring.

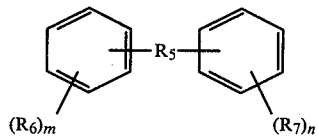
(V)

wherein $R_5$ is an alkenylene group or a cycloalkenylene group, and the aliphatic unsaturated double bond thereof is not conjugated with the aromatic nuclei, m and n are integers from 0 to 3, and $R_6$ of m in number and $R_7$ of n in number are the same or different from each other and each of them is a hydrogen atom or an alkyl group.

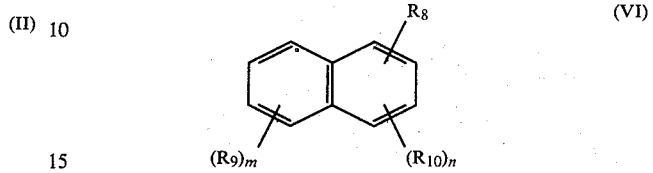
(VI)

wherein $R_8$ is an alkenyl group or a cycloalkenyl group, m and n are integers from 0 to 3, $R_9$ of m in number and $R_{10}$ of n in number are the same or different from each other, and each of them is a hydrogen atom or an alkyl group.

12. The oil-filled electrical appliance in claim 7, wherein said aromatic diolefins are the compounds represented by the following general formulae (VII) to (IX):

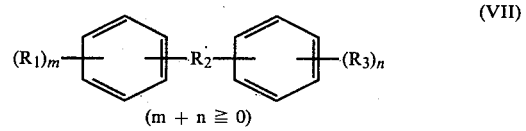
(VII)

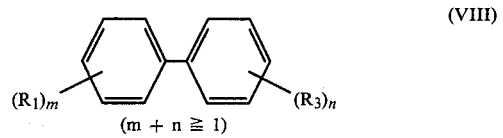
(VIII)

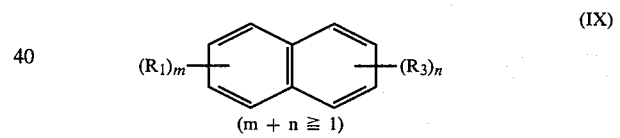
(IX)

wherein $R_1$, $R_2$ and $R_3$ are hydrocarbon residual groups, each of m and n is 0 (zero) or a positive integer, $R_1$ of m in number, $R_2$, and $R_3$ of n in number are either the same or different substituent groups, and the total number of double bonds in the substituent groups is 2 in each formula.

13. The oil-filled electrical appliance in claim 7, wherein said electrical appliance is one member selected from the group consisting of oil-filled capacitors, oil-filled cables and transformers.

14. The oil-filled electrical appliance in claim 7, wherein the insulating material or dielectric material used in said oil-filled electrical appliance is insulating paper, synthetic resin film or their combination.

15. The oil-filled electrical appliance in claim 14, wherein said synthetic resin film is polyethylene film or polypropylene film.

* * * * *